US012788730B1

(12) United States Patent
Tabuteau

(10) Patent No.: US 12,788,730 B1
(45) Date of Patent: Nov. 10, 2026

(54) MICROPARTICLES CONTAINING BUPROPION

(71) Applicant: AXSOME THERAPEUTICS, INC., New York, NY (US)

(72) Inventor: Herriot Tabuteau, New York, NY (US)

( * ) Notice: Subject to any disclaimer, the term of this patent is extended or adjusted under 35 U.S.C. 154(b) by 0 days.

(21) Appl. No.: 19/204,430

(22) Filed: May 9, 2025

Related U.S. Application Data

(63) Continuation of application No. 18/512,632, filed on Nov. 17, 2023, now abandoned, which is a continuation of application No. 18/162,259, filed on Jan. 31, 2023, now abandoned.

(60) Provisional application No. 63/370,778, filed on Aug. 8, 2022, provisional application No. 63/370,572, filed on Aug. 5, 2022, provisional application No. 63/357,355, filed on Jun. 30, 2022.

(51) Int. Cl.

| | |
|---|---|
| ***A61K 9/20*** | (2006.01) |
| ***A61K 9/14*** | (2006.01) |
| ***A61K 31/137*** | (2006.01) |

(52) U.S. Cl.
CPC ............ *A61K 31/137* (2013.01); *A61K 9/145* (2013.01); *A61K 9/146* (2013.01)

(58) Field of Classification Search
CPC .......... A61K 9/20; A61K 9/2004; A61K 9/50; A61K 9/501; A61K 9/5021; A61K 9/5042; A61K 9/5092; A61K 9/5107
See application file for complete search history.

(56) References Cited

U.S. PATENT DOCUMENTS

| | | | |
|---|---|---|---|
| 4,008,719 | A | 2/1977 | Theeuwes et al. |
| 4,393,078 | A | 7/1983 | Peck |
| 4,425,363 | A | 1/1984 | Stern |
| 4,434,449 | A | 2/1984 | Dickey |
| 4,438,138 | A | 3/1984 | Stern |
| 4,507,323 | A | 3/1985 | Stern |
| 4,571,395 | A | 2/1986 | Peck |
| 4,798,826 | A | 1/1989 | Peck |
| 4,835,147 | A | 5/1989 | Roberts |
| 4,895,845 | A | 1/1990 | Seed |
| 4,935,429 | A | 6/1990 | Dackis et al. |
| 5,166,207 | A | 11/1992 | Smith |
| 5,217,987 | A | 6/1993 | Berger |
| 5,447,948 | A | 9/1995 | Seibyl et al. |
| 5,753,712 | A | 5/1998 | Pinkser |
| 6,150,420 | A | 11/2000 | Houdi et al. |
| 6,306,436 | B1 | 10/2001 | Chungi et al. |
| 6,337,328 | B1 | 1/2002 | Fang et al. |
| 6,458,374 | B1 | 10/2002 | McCullough et al. |
| 6,495,605 | B2 | 12/2002 | Mccullough et al. |
| 9,198,905 | B2 | 12/2015 | Tabuteau |
| 9,314,462 | B2 | 4/2016 | Tabuteau |
| 9,408,815 | B2 | 8/2016 | Tabuteau |
| 9,457,025 | B2 | 10/2016 | Tabuteau |
| 9,474,731 | B1 | 10/2016 | Tabuteau |
| 9,700,528 | B2 | 7/2017 | Tabuteau |
| 9,707,191 | B2 | 7/2017 | Tabuteau |
| 9,732,031 | B2 | 8/2017 | DeWitt et al. |
| 9,763,932 | B2 | 9/2017 | Tabuteau |
| 9,861,595 | B2 | 1/2018 | Tabuteau |
| 9,968,568 | B2 | 5/2018 | Tabuteau |
| 10,080,727 | B2 | 9/2018 | Tabuteau |
| 10,251,879 | B2 | 4/2019 | Tabuteau |
| 10,512,643 | B2 | 12/2019 | Tabuteau |
| 10,695,304 | B2 | 6/2020 | Tabuteau |
| 10,983,316 | B2 | 4/2021 | Tang et al. |
| 11,179,351 | B2 | 11/2021 | Tabuteau |
| 11,179,352 | B2 | 11/2021 | Tabuteau |
| 11,291,639 | B2 | 4/2022 | Tabuteau |
| 11,331,285 | B2 | 5/2022 | Tabuteau |
| 11,344,513 | B2 | 5/2022 | Tabuteau |
| 11,344,514 | B2 | 5/2022 | Tabuteau |
| 11,433,035 | B2 | 9/2022 | Tabuteau |
| 11,660,273 | B2 | 5/2023 | Tabuteau |
| 11,660,274 | B2 | 5/2023 | Tabuteau |
| 11,786,488 | B2 | 10/2023 | Tabuteau |
| 2001/0011103 | A1 | 8/2001 | McCullough et al. |
| 2002/0052341 | A1 | 5/2002 | Fang et al. |
| 2003/0096873 | A1 | 5/2003 | McCullough et al. |
| 2006/0167032 | A1 | 7/2006 | Galer et al. |
| 2010/0291225 | A1 | 11/2010 | Fanda et al. |
| 2015/0126541 | A1 | 5/2015 | Tabuteau |

(Continued)

FOREIGN PATENT DOCUMENTS

| | | |
|---|---|---|
| CA | 2318921 | 8/1999 |
| CL | 200502581 | 6/2006 |

(Continued)

OTHER PUBLICATIONS

Coles et al., "Stereoselective Metabolism of Bupropion by Cytochrome P4502B6 (CYP2B6) and Human Liver Microsomes", Pharmaceutical Research, 25(6), 1405-1411, Jun. 2008.

(Continued)

*Primary Examiner* — Micah Paul Young
(74) *Attorney, Agent, or Firm* — Procopio, Cory, Hargreaves & Savitch LLP; Brent Johnson; "Raph" Younghoon Kim

(57) ABSTRACT

This disclosure relates to microparticles containing bupropion, e.g., microparticles having a particle diameter of about 50 μm to about 100 μm. These microparticles may be included in pharmaceutical compositions and/or dosage forms for treatment of various disease, such as depression.

16 Claims, No Drawings

(56) References Cited

U.S. PATENT DOCUMENTS

| | | | | |
|---|---|---|---|---|
| 2016/0030420 | A1 | 2/2016 | Tabuteau | |
| 2016/0199321 | A1 | 7/2016 | Tabuteau | |
| 2016/0263100 | A1 | 9/2016 | Tabuteau | |
| 2016/0311757 | A1 | 10/2016 | DeWitt et al. | |
| 2016/0317476 | A1 | 11/2016 | Tabuteau | |
| 2016/0375008 | A1 | 12/2016 | Tabuteau | |
| 2017/0007558 | A1 | 1/2017 | Tabuteau | |
| 2017/0014357 | A1 | 1/2017 | Tabuteau | |
| 2017/0304229 | A1 | 10/2017 | Tabuteau | |
| 2017/0304230 | A1 | 10/2017 | Tabuteau | |
| 2017/0369420 | A1 | 12/2017 | DeWitt et al. | |
| 2018/0092906 | A1 | 4/2018 | Tabuteau | |
| 2019/0216800 | A1 | 7/2019 | Tabuteau | |
| 2019/0216801 | A1 | 7/2019 | Tabuteau | |
| 2019/0219800 | A1 | 7/2019 | Tang et al. | |
| 2020/0093760 | A1 | 3/2020 | Tabuteau | |
| 2020/0093761 | A1 | 3/2020 | Tabuteau | |
| 2020/0197331 | A1 | 6/2020 | Tabuteau | |
| 2020/0197333 | A1 | 6/2020 | Tabuteau | |
| 2020/0222339 | A1 | 7/2020 | Tabuteau | |
| 2020/0222342 | A1 | 7/2020 | Tabuteau | |
| 2020/0315992 | A1 | 10/2020 | Tabuteau | |
| 2020/0338021 | A1 | 10/2020 | Tabuteau | |
| 2020/0345664 | A1 | 11/2020 | Tabuteau | |
| 2021/0177834 | A1 | 6/2021 | Tabuteau | |
| 2021/0196704 | A1 | 7/2021 | Tabuteau | |
| 2021/0330613 | A1 | 10/2021 | Tabuteau | |
| 2022/0193011 | A1 | 6/2022 | Tabuteau | |
| 2022/0249405 | A1 | 8/2022 | Tabuteau | |
| 2022/0249406 | A1 | 8/2022 | Tabuteau | |
| 2022/0257538 | A1 | 8/2022 | Tabuteau | |
| 2023/0248668 | A1 | 8/2023 | Tabuteau | |
| 2023/0248669 | A1 | 8/2023 | Tabuteau | |
| 2023/0414538 | A1 | 12/2023 | Tabuteau | |
| 2024/0000729 | A1 * | 1/2024 | Tabuteau | A61K 9/146 |

FOREIGN PATENT DOCUMENTS

| | | | | |
|---|---|---|---|---|
| CL | 200603299 | | 6/2017 | |
| CN | 1819821 | A | 8/2006 | |
| EC | SP-05-6216 | | 12/2005 | |
| EC | SP-07-7999 | | 12/2007 | |
| EC | SP-2010-9923 | | 2/2010 | |
| EC | SP-2010-10144 | | 4/2010 | |
| EC | 2020-60179 | | 9/2020 | |
| EC | 2020-82568 | | 12/2020 | |
| EP | 3666271 | A1 * | 6/2020 | A61K 31/5383 |
| JP | 2003529563 | | 10/2003 | |
| JP | 2022124557 | A | 8/2022 | |
| MX | 2013014166 | A | 6/2015 | |
| WO | 1999038502 | A1 | 8/1999 | |
| WO | 2001062257 | A2 | 8/2001 | |
| WO | 2004/089873 | A1 | 10/2004 | |
| WO | WO-2009050726 | A2 * | 4/2009 | A61K 9/0043 |
| WO | 2012118562 | A1 | 9/2012 | |
| WO | 2015095713 | A1 | 6/2015 | |
| WO | 2019165379 | A1 | 8/2019 | |

OTHER PUBLICATIONS

Joy et al., "Use of Enantiomeric Bupropion and Hydroxybupropion to Assess CYP2B6 Activity in Glomerular Kidney Diseases", Journal of Clinical Pharmacology, 50 (6), 714-720, Jun. 2010.

Written Opinion of the International Search Authority for PCT/US2014/071519 (corresponding to WO2015095713) dated Feb. 10, 2015.

Malik et al., "Enantioseparation of (RS)-Bupropion and determination of configuration", Journal of Liquid Chromatography & Related Technologies, 41(4), 155-160, 2018.

Masters et al., "Chiral plasma pharmacokinetics and urinary excretion of bupropion and metabolites in healthy volunteers", Journal of Pharmacology and Experimental Therapeutics, 358(2), 230-238, 2016.

Sager et al., "Stereoselective metabolism of bupropion to OH-bupropion, threohydrobupropion, erythrohydrobupropion, and 4'-OH-bupropion in vitro", Drug Metabolism & Disposition, 44(10), 1709-1719, 2016.

Sager et al., "In vitro to in vivo extrapolation of the complex drug-drug interaction of bupropion and its metabolites with CYP2D6; simultaneous reversible inhibition and CYP2D6 downregulation", Biochemical Pharmacology (Amsterdam, Netherlands), 123, 85-96, 2017.

Teitelbaum et al., "Development, validation and application of a comprehensive stereoselective LC/MS-MS assay for bupropion and oxidative, reductive, and glucuronide metabolites in human urine", Journal of Chromatography B: Analytical Technologies in the Biomedical and Life Sciences, 1027, 239-253, 2016.

Teitelbaum et al., "Development and validation of a high-throughput stereoselective LC-MS/MS assay for bupropion, hydroxybupropion, erythrohydrobupropion, and threohydrobupropion in human plasma", Journal of Chromatography B: Analytical Technologies in the Biomedical and Life Sciences, 1017-1018, 101-113, 2016.

Masters et al., "Stereoselective method to quantify bupropion and its three major metabolites, hydroxybupropion, erythro-dihydrobupropion, and threo-dihydrobupropion using HPLC-MS/MS", Journal of Chromatography B: Analytical Technologies in the Biomedical and Life Sciences, 1015-1016, 201-208, 2016.

Bagatin et al., "Molecular docking and panicolytic effect of 8-prenylnaringenin in the elevated T-maze", Chemical & Pharmaceutical Bulletin, 62(12), 1231-1237, 2014.

Batra et al., "Enantioresolution of (RS)-bupropion by reversed-phase high-performance liquid chromatography using cyanuric chloride based chiral derivatizing reagents having amino acids as chiral auxiliaries", Journal of Liquid Chromatography & Related Technologies, 37(17), 2515-2528, 2014.

Meyer et al., "Formation of threohydrobupropion from bupropion is dependent on 11ß-hydroxysteroid dehydrogenase 1", Drug Metabolism & Disposition, 41(9), 1671-1678, 2013.

Bhushan et al., "High-performance liquid chromatographic enantioseparation of (RS)-bupropion using isothiocyanate-based chiral derivatizing reagents", Biomedical Chromatography, 27(8), 956-959, 2013.

Perera et al., "Screening approach, optimization and scale-up for chiral liquid chromatography of cathinones", Journal of Chromatography A, 1269, 189-197, 2012.

Arias et al., "Structural and functional interaction of (+)-2-(N-tert-butylamino)-3'-iodo-4'-azidopropiophenone, a photoreactive bupropion derivative, with nicotinic acetylcholine receptors", Neurochemistry International, 61(8), 1433-1441, 2012.

Zhou et al., "CE enantioseparation of bupropion hydrochloride", Yaowu Fenxi Zazhi, 32(6), 990-993, 972, 2012.

Lai et al., "Novel cyclodextrin chiral stationary phases for high performance liquid chromatography enantioseparation: Effect of cyclodextrin type", Journal of Chromatography A, 1218(33), 5597-5601, 2011.

Castro-Puyana et al., "Sensitized phosphorescence as detection method for the enantioseparation of bupropion by capillary electrophoresis", Electrophoresis, 31(23-24), 3928-3936, 2010.

Castro-Puyana et al., "Enantiomeric separation of bupropion enantiomers by electrokinetic chromatography: Quantitative analysis in pharmaceutical formulations", Journal of Chromatography B: Analytical Technologies in the Biomedical and Life Sciences, 875(1), 260-265, 2008.

Kharasch et al., "Rapid clinical induction of hepatic cytochrome P450 2B6 activity by ritonavir", Antimicrobial Agents and Chemotherapy, 52(5), 1663-1669, 2008.

Kharasch et al., "Stereoselective bupropion hydroxylation as an in vivo phenotypic probe for cytochrome P4502B6 (CYP2B6) activity", Journal of Clinical Pharmacology, 48(4), 464-474, 2008.

Moda et al., "In silico prediction of human plasma protein binding using hologram QSAR", Letters in Drug Design & Discovery, 4(7), 502-509, 2007.

Moda et al., "Hologram QSAR model for the prediction of human oral bioavailability", Bioorganic & Medicinal Chemistry, 15(24), 7738-7745, 2007.

(56) References Cited

OTHER PUBLICATIONS

Coles et al., "Stereoselective analysis of bupropion and hydroxybupropion in human plasma and urine by LC/MS/MS", Journal of Chromatography B: Analytical Technologies in the Biomedical and Life Sciences, 857(1), 67-75, 2007.
Liu et al., "Preparation and evaluation of 2,6-di-O-pentyl-ß-cyclodextrin bonded silica stationary phase for high performance liquid chromatography", Sepu, 22(6), 630-633, 2004.
Li et al., "Single-isomer sulfated a-cyclodextrins for capillary electrophoresis. Part 2. Hexakis(6-O-sulfo)-α-cyclodextrin: Synthesis, analytical characterization, and initial screening tests", Electrophoresis, 25(9), 1201-1210, 2004.
Busby et al., "Nonaqueous capillary electrophoretic separation of basic enantiomers using octakis(2,3-O-dimethyl-6-O-sulfo)-γ-cyclodextrin, a new, single-isomer chiral resolving agent", Electrophoresis, 23(3), 456-461, 2002.
Fang et al., "Rapid access to enantiopure bupropion and its major metabolite by stereospecific nucleophilic substitution on an α-keto triflate", Tetrahedron: Asymmetry, 11(18), 3659-3663, 2000.
Steuer et al., "Impact of Cytochrome P450 2D6 Function on the Chiral Blood Plasma Pharmacokinetics of 3,4-Methylenedioxymethamphetamine (MDMA) and Its Phase I and II Metabolites in Humans", PLOS ONE | DOI: 10.1371/journal.pone.0150955, Mar. 11, 2016.
International Search Report and Written Opinion of the International Searching Authority dated Jul. 11, 2019, corresponding to international patent application No. PCT/US2019/019445.
International Preliminary Report on Patentability from the International Bureau dated Sep. 3, 2020, corresponding to international patent application No. PCT/US2019/019445.
International Search Report and Written Opinion of the International Searching Authority dated Dec. 30, 2019, corresponding to international patent application No. PCT/US2019/052210.
International Preliminary Report on Patentability from the International Bureau dated Apr. 1, 2021, corresponding to international patent application No. PCT/US2019/052210.
International Search Report and Written Opinion of the International Searching Authority dated Nov. 13, 2020, corresponding to international patent application No. PCT/US2020/046755.
Reimherr et al., Bupropion SR in adults with ADHD: a short-term, placebo-controlled trial. Neuropsychiatric Disease And Treatment, 1(3), 245-251, Sep. 2005.
Chilean Search Report mailed on Nov. 15, 2021 for Chilean Patent Application No. 202002166.
Communication of Notices of Opposition over Ecuador Patent No. SENADI-2022-66161 from Ecuador Patent Office on Dec. 8, 2022.
Musso, David L., et al. "Synthesis and evaluation of the antidepressant activity of the enantiomers of bupropion." Chirality 5.7 (1993): 495-500.
"Dosage form" Wikipedia, the free encyclopedia, https://ja.wikipedia.org/wiki/剤形, retrieved on Sep. 8, 2023.
Damaj, M. Imad, et al., "Enantioselective effects of hydroxy metabolites of bupropion on behavior and on function of monoamine transporters and nicotinic receptors." Mol. Pharmacol., 2004, vol. 66, No. 3, pp. 675-682, DOI: 10.1124/mol.104.001313.
Damaj, M. Imad, et al., "Effects of Hydroxymetabolites of Buproprion on Nicotine Dependence Behavior in Mice." J. Pharmacol. Exp. Ther., 2010, vol. 334, No. 3, pp. 1087-1095, DOI: 10.1124/jpet.110.166850.
Hansard, Matthew J., et al., "A major metabolite of buproprion reverses motor deficits in 1-methyl-4-phsnyl-1,2,3,6-tetrahydropyridine-treated common marmosets." Behavioural Pharmacology, 2011, vol. 22, No. 3, pp. 269-274, DOI: 10.1097/FBP.0b013e328345ca37.
Kotlyar M, Brauer LH, Tracy TS, Hatsukami DK, Harris J, Bronars CA, Adson DE. Inhibition of CYP2D6 activity by bupropion. J Clin Psychopharmacol. Jun. 2005;25(3): 226-9. doi: 10.1097/01.jcp.0000162805.46453.e3.
English translation of Office Action BR 11 2020 017179 4 dated Feb. 15, 2024, 3 pages.
English translation of Office Action BR 11 2022 005045 3 dated Aug. 20, 2024, 3 pages.
English translation of Office Action JP 2022-124557 dated Jun. 11, 2024, 4 pages.
English translation of Office Action CN 202080065520.4 dated Oct. 8, 2024, 2 pages.
International Search Report and Written Opinion of the International Searching Authority dated Aug. 28, 2023, corresponding to international patent application No. PCT/US2023/069367.

* cited by examiner

MICROPARTICLES CONTAINING BUPROPION

BACKGROUND

Bupropion is FDA approved for the treatment of depression and smoking cessation.

SUMMARY

This disclosure relates to microparticles containing bupropion. It has been found that the particle size of a microparticle containing bupropion can affect the dissolution profile of bupropion in the microparticle. This may also affect the pharmacokinetics of bupropion.

Some embodiments include a microparticle comprising bupropion hydrochloride, wherein the microparticle has a particle diameter of about 50 μm to about 100 μm; the particle diameter may be determined by laser diffraction or other suitable techniques.

Some embodiments include a dosage form comprising microparticles containing bupropion, wherein at least 80% of the microparticles have a particle diameter of about 1 μm to about 300 μm as determined by laser diffraction.

Some embodiments include a pharmaceutical composition comprising microparticles containing bupropion, wherein at least 80% of the microparticles have a particle diameter of about 1 μm to about 300 μm; the particle diameter may be determined by laser diffraction or other suitable techniques.

DETAILED DESCRIPTION

A microparticle containing bupropion may include, or be prepared from, any suitable form of bupropion, such as a salt form, e.g., bupropion hydrochloride, the free base form, hydrates, solvates, polymorphs, other solid forms, etc. In some embodiments, the microparticle, or a dosage form or a pharmaceutical composition containing the microparticle, is free of any other active pharmaceutical agents. In some embodiments, the microparticle may be present in a dosage form that also contains a dextromethorphan in any suitable form, such as a salt form, the free base form, hydrates, solvates, polymorphs, other solid forms, etc.

The microparticles may contain any suitable amount of the bupropion. For example, the bupropion, e.g., bupropion hydrochloride may comprise about 1-20%, about 20-40%, about 10-20%, about 15-20%, about 20-25%, about 25-30%, about 30-35%, about 35-40%, about 40-60%, about 60-80%, about 80-100%, about 20-30%, about 30-33%, or about 31-32% of the weight of the microparticles.

When prepared in certain ways, microparticles may be present in a distribution of size. This distribution of size may be described in a variety of ways, but one convenient description is to identify the $10^{th}$ percentile of microparticle diameter, the median microparticle diameter, and the $90^{th}$ percentile of microparticle diameter.

The 10th percentile of microparticle diameter is the size where 10% of the microparticles are of that diameter or smaller. In some embodiments, the $10^{th}$ percentile of microparticle diameter is about 1-30 μm, about 1-3 μm, about 3-5 am, about 5-10 μm, about 10-15 μm, about 15-20 μm, about 20-25 μm, or about 25-30 μm; the particle diameter may be determined by laser diffraction or other suitable techniques.

The median microparticle diameter is the diameter where the number of particles that are smaller than the median microparticle diameter is equal to the number of particles that are larger than the median microparticle diameter. In some embodiments, the microparticles have a median particle diameter of about 50-100 μm, about 50-55 μm, about 55-60 μm, about 60-65 μm, about 65-70 μm, about 70-75 μm, about 75-80 μm, about 80-85 μm, about 85-90 μm, about 90-95 μm, about 95-100 μm, about 50-60 μm, about 60-70 μm, about 70-80 μm, about 80-90 μm, about 90-100 μm, about 50-75 μm, or about 75-100 μm; the particle diameter may be determined by laser diffraction or other suitable techniques.

The$_{90t}$h percentile of microparticle diameter is the size where 90% of the microparticles are of that diameter or smaller. In some embodiments, $90^{th}$ percentile of microparticle diameter is about 200-300 μm, about 200-210 μm, about 210-220 μm, about 220-230 μm, about 230-240 μm, about 240-250 μm, about 250-260 μm, about 260-270 μm, about 270-280 μm, about 280-290 μm, about 290-300 μm, about 200-240 μm, about 240-270 μm, or about 270-300 μm; the particle diameter may be determined by laser diffraction or other suitable techniques.

The particle size distribution may also be characterized as a range of particle sizes, such as particle diameters, within which at least about 80% (e.g., at least particles from the $10^{th}$ to the $90^{th}$ percentile) of the microparticles would fall. In some embodiments, at least about 80% of the microparticles have a particle diameter of about 1-300 μm, about 2-260 μm, or about 20-230 μm; the particle diameter may be determined by laser diffraction or other suitable techniques.

The particle size distribution may be further characterized by the ratio between the particle size of the $90^{th}$ percentile of microparticle diameter and the median microparticle diameter, the ratio between the particle size of the median and the $10^{th}$ percentile of microparticle diameter, and the ratio between the $90^{th}$ percentile of microparticle diameter and the $10^{th}$ percentile of microparticle diameter.

In some embodiments, the ratio between the $90^{th}$ percentile of microparticle diameter and the median microparticle diameter is about 2-10 (e.g., if the $90^{th}$ percentile has a diameter that is twice that of the median, the ratio is 2), about 2-3, about 3-4, about 4-5, about 5-6, about 6-7, about 7-8, about 8-9, about 9-10, about 2-4, about 4-6, about 6-8, about 8-10, about 2-6, or about 6-10.

In some embodiments, the ratio between the median microparticle diameter and the $10^{th}$ percentile of microparticle diameter is about 2-50, about 2-6, about 6-10, about 10-15, about 15-20, about 20-25, about 25-30, about 30-35, about 35-40, about 40-45, about 45-50, about 2-10, about 10-20, about 20-30, about 30-40, about 40-50, about 2-20, or about 20-50.

In some embodiments, the ratio between the $90^{th}$ percentile of microparticle diameter and the $10^{th}$ percentile of microparticle diameter is about 5-200, about 5-20, about 20-40, about 40-60, about 60-80, about 80-100, about 100-120, about 120-140, about 140-160, about 160-180, about 180-200, about 5-50, about 50-120, or about 120-200.

The microparticles may be formulated into a pharmaceutical composition or a dosage form. In some embodiments, the microparticles, pharmaceutical composition, or dosage form may comprise a stabilizer, such as cysteine. The pharmaceutical composition may include any suitable amount of stabilizer, such as about 1-30 mg, about 30-100 mg, about 30-40 mg, about 40-50 mg, about 50-60 mg, about 60-70 mg, about 70-80 mg, about 80-90 mg, about 90-100 mg, or about 65-70 mg of the stabilizer.

The microparticles, pharmaceutical composition, or dosage form may further comprise a sustained release or controlled release polymer, such as a crosslinked or uncross linked acrylate polymer or copolymer (e.g., a carbomer copolymer Type A such as Carbopol 971P), a cellulose derivative, such as methylcellulose, etc. In some embodiments, the controlled release polymer is about 1-40%, about 1-5%, about 5-10%, about 10-15%, about 15-20%, about 20-30%, about 30-40%, about 11-13%, or about 12% of the weight of the pharmaceutical composition. In some embodiments, the controlled release polymer is about 0.1-20%, about 0.1-2%, about 2-4%, about 4-6%, about 6-8%, about 8-10%, about 10-15%, about 15-20%, or about 7% of the weight of the dosage form.

The microparticles, pharmaceutical composition, or dosage form may further comprise a filler such as microcrystalline cellulose. In some embodiments, the filler may be about 20-60%, about 20-30%, about 30-40%, about 40-50%, or about 50-60% of the weight of the pharmaceutical composition or the dosage form.

The microparticles, pharmaceutical composition, or dosage form may further comprise a lubricant such as magnesium stearate. In some embodiments, the lubricant is about 0.1-10%, about 0.1-2%, about 2-4%, about 4-6%, about 6-8%, or about 8-10% of the weight of the pharmaceutical composition or the dosage form.

The dosage form may be formulated for any suitable route of administration, such as oral administration.

Dosage forms, such as solid dosage forms, e.g., capsules, tablets, or pills, for oral administration may also contain one or more of the following: a binder such as gum tragacanth, acacia, corn starch, or gelatin; an excipient, such as dicalcium phosphate; a disintegrating agent such as corn starch, potato starch, alginic acid, and the like; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as a coating, for example, tablets, pills, or capsules may be coated with shellac, sugar, or both. It may be desirable for material in a dosage form or pharmaceutical composition to be pharmaceutically pure and nontoxic in the amounts employed.

The dosage form may further contain a second active pharmaceutical ingredient, such as dextromethorphan, e.g., dextromethorphan hydrobromide. In some embodiments, the dosage form may contain bupropion and dextromethorphan, and no other active pharmaceutical ingredients. In some embodiments, the bupropion and the dextromethorphan are in two different layers or phases of the dosage form, e.g., each layer contains only bupropion or dextromethorphan and none of the other.

In some embodiments, the dosage form contains cysteine, Carbopol 971P, microcrystalline cellulose, silicon dioxide, and magnesium. In some embodiments, the dosage form contains a first layer comprising bupropion and cysteine, and a second layer comprising dextromethorphan, microcrystalline cellulose, croscarmellose sodium, and magnesium stearate.

An example of the composition of microparticles containing bupropion is shown below.

Composition 1

| Ingredient | Amount (mg) |
|---|---|
| Bupropion | 90-120 |
| Cysteine | 1-100 |

-continued

Composition 1

| Ingredient | Amount (mg) |
|---|---|
| Carbopol 971P | 20-60 |
| Microcrystalline Cellulose | 200-300 |

Microparticles, such as microparticles shown above, may be formed into a layer in a tablet or dosage form, e.g., by pressing. They could also be enclosed within a capsule.

In some embodiments, a dosage form may contain microparticles containing bupropion and a second therapeutically active agent, such as dextromethorphan. In some embodiments, such a dosage form contains no other therapeutically active agent than bupropion and dextromethorphan.

In dosage forms that include dextromethorphan, the dextromethorphan may be incorporated into composition 2.

Composition 2

| Ingredient | Amount (mg) |
|---|---|
| Dextromethorphan | 30-60 |
| Microcrystalline Cellulose | 100-150 |
| Croscarmellose sodium | 1-20 |
| Magnesium Stearate | 1-10 |

Composition 1 and Composition 2 may be, e.g., in two separate layers in a tablet, may be two separate powders contained in a capsule, etc. Other types of dosage forms may also be formed from Composition 1 and Composition 2.

Microparticles described herein may be prepared, for example, by screening bupropion, cysteine, Carbopol 971, and Microcrystalline Cellulose from Composition 1 (e.g., through 20 mesh), mixing, spray granulating, drying, and milling the dried blend. The resulting particle size distribution can be determined by laser diffraction.

The microparticles, pharmaceutical compositions, or dosage forms, described herein may be useful in treating neurological or psychiatric conditions, such as depression, including major depressive disorder or treatment-resistant major depressive disorder, agitation, such as agitation associated with Alzheimer's disease, addiction, such as nicotine addiction, etc.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, hitting (including self), Kicking, grabbing onto people, pushing, throwing things, biting, scratching, spitting, hurting self or others, tearing things or destroying property, making physical sexual advances, pacing, aimless wandering, inappropriate dress or disrobing, trying to get to a different place, intentional falling, eating/drinking inappropriate substances, handling things inappropriately, hiding things, hoarding things, performing repetitive mannerisms, general restlessness, screaming, making verbal sexual advances, cursing or verbal aggression, repetitive sentences or questions, strange noises (weird laughter or crying), complaining, negativism, constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barre syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, but are not limited to, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited to, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating" or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

The following documents are incorporated by reference herein in their entireties: MEDICATION GUIDE for AUVELITY™ (www.axsome.com/auvelity-medication-guide.pdf), HIGHLIGHTS OF PRESCRIBING INFORMA- TION for AUVELITY™ (www.axsome.com/auvelity-prescribing-information.pdf), and U.S. Provisional Application Nos. 63/357,355, filed Jun. 30, 2022; 63/370,572, filed Aug. 5, 2022; and 63/370,778, filed Aug. 8, 2022.

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A kit comprising a first dosage form comprising about 105 mg of bupropion hydrochloride, or a molar equivalent amount of another salt form of bupropion or the free base form of bupropion, and about 30 mg of dextromethorphan, or a molar equivalent amount of another salt form of dextromethorphan or the free base form of dextromethorphan; and a second dosage form comprising about 105 mg of bupropion hydrochloride, or a molar equivalent amount of another salt form of bupropion or the free base form of bupropion, and about 45 mg of dextromethorphan, or a molar equivalent amount of another salt form of dextromethorphan or the free base form of dextromethorphan, wherein the first dosage form or the second dosage form contains a plurality of microparticles, wherein the plurality of microparticles has a median particle diameter of about 50 μm to about 100 μm as determined by laser diffraction, wherein the 10th percentile of microparticle diameter of the plurality of microparticles is about 1 μm to about 30 μm as determined by laser diffraction, and wherein the 90th percentile of microparticle diameter of the plurality of microparticles is about 200 μm to about 300 μm as determined by laser diffraction.

2. The kit of claim 1, wherein the bupropion hydrochloride contained in the first dosage form or second dosage form comprises about 30% to about 35% of the weight of the plurality of microparticles.

3. A dosage form comprising microparticles containing from about 90 mg to about 120 mg of bupropion hydrochloride, or a molar equivalent amount of another salt form of bupropion or the free base form of bupropion; and from about 30 mg to about 60 mg of dextromethorphan hydrobromide, or a molar equivalent amount of another salt form of dextromethorphan or the free base form of dextromethorphan, wherein at least about 80% of the microparticles have a particle diameter of about 1 μm to about 300 μm as determined by laser diffraction, wherein the 10th percentile of microparticle diameter of the microparticles is about 1 μm to about 30 μm as determined by laser diffraction, and wherein the 90th percentile of microparticle diameter of the microparticles is about 200 μm to about 300 μm as determined by laser diffraction.

4. The dosage form of claim 3, wherein the median microparticle diameter is about 50 μm to about 100 μm as determined by laser diffraction.

5. The dosage form of claim 4, wherein the $90^{th}$ percentile of microparticle diameter of the microparticles is about 2 times to about 10 times the median microparticle diameter of the microparticles as determined by laser diffraction.

6. The dosage form of claim 4, wherein the median particle diameter of the microparticles is about 2 times to about 50 times the $10^{th}$ percentile of microparticle diameter of the microparticles as determined by laser diffraction.

7. The dosage form of claim 4, wherein the $90^{th}$ percentile of microparticle diameter of the microparticles is about 5 to about 200 times the $10^{th}$ percentile of microparticle diameter of the microparticles as determined by laser diffraction.

8. The dosage form of claim 4, further comprising microcrystalline cellulose.

9. A pharmaceutical composition comprising microparticles containing from about 90 mg to about 120 mg of bupropion hydrochloride, or a molar equivalent amount of another salt form of bupropion or the free base form of bupropion; and from about 30 mg to about 60 mg of dextromethorphan hydrobromide, or a molar equivalent amount of another salt form of dextromethorphan or the free base form of dextromethorphan, wherein at least 80% of the microparticles have a particle diameter of about 1 μm to about 300 μm as determined by laser diffraction, wherein the 10th percentile of microparticle diameter of the microparticles is about 1 μm to about 30 μm as determined by laser diffraction.

10. The pharmaceutical composition of claim 9, wherein the microparticles containing bupropion have a median particle diameter of about 50 μm to about 100 μm as determined by laser diffraction.

11. The pharmaceutical composition of claim 9, wherein the $90^{th}$ percentile of microparticle diameter of the microparticles is about 200 μm to about 300 μm as determined by laser diffraction.

12. The pharmaceutical composition of claim 9, wherein the $90^{th}$ percentile of microparticle diameter of the microparticles is about 2 times to about 10 times the median microparticle diameter as determined by laser diffraction.

13. The pharmaceutical composition of claim 9, wherein the median particle diameter of the microparticles is about 2 times to about 50 times the $10^{th}$ percentile of microparticle diameter as determined by laser diffraction.

14. The pharmaceutical composition of claim 9, wherein the $90^{th}$ percentile of microparticle diameter of the microparticles is about 5 to about 200 times the $10^{th}$ percentile of microparticle diameter as determined by laser diffraction.

15. The pharmaceutical composition of claim 9, further comprising a sustained release or controlled release polymer.

16. The pharmaceutical composition of claim 9, further comprising magnesium stearate.

* * * * *